United States Patent [19]

Schoellkopf et al.

[11] Patent Number: 5,157,145

[45] Date of Patent: Oct. 20, 1992

[54] PROCESS FOR THE PREPARATION OF DIPEPTIDES WITH C-TERMINAL NON-PROTEINOGENOUS AMINO ACIDS

[75] Inventors: Ulrich Schoellkopf, Bovenden; Ulrich Groth, Goettingen; Meinolf Lange, Waake-Boesinghausen, all of Fed. Rep. of Germany

[73] Assignee: BASF Aktiengesellschaft, Ludwigshafen, Fed. Rep. of Germany

[21] Appl. No.: 466,445

[22] PCT Filed: Sep. 9, 1989

[86] PCT No.: PCT/EP89/01050

§ 371 Date: Jul. 17, 1990

§ 102(e) Date: Jul. 17, 1990

[87] PCT Pub. No.: WO90/03386

PCT Pub. Date: Apr. 5, 1990

[30] Foreign Application Priority Data

Sep. 17, 1988 [DE] Fed. Rep. of Germany ....... 3831716

[51] Int. Cl.$^5$ ................. C07C 229/26; C07C 229/36
[52] U.S. Cl. ....................................... 560/41; 544/408
[58] Field of Search .......................................... 560/41

[56] References Cited

PUBLICATIONS

Chemical Abstracts, vol. 108, No. 9, Feb. 29, 1988, (Columbus, Ohio, US), U. Schoellkopf et al.: "Asymmetric syntheses via heterocyclic intermediates, XXXVI. Asymmetric synthesis of dimethyl (R)-4-amino-4-methyl-2-penetendioates(dimethyl B, y-didehydro-d-methyl-D-glutamates) or methyl (R)-2, 5-dihydro-2-methyl-5-oxo-2-pyrrolecarboxylates by the bislactim ether method. Studies on the asymmetric synthesis of B,y-didehydroglutamic acids", see p. 726, abstract 75801u, & Liebigs Ann, Chem. 1988, (1) 87-92.

Chemical Abstracts, vol. 109, No. 17, Oct. 24, 1988, (Columbus, Ohio, US), U. Schoellkopf et al.: "Asymmetric synthesis via heterocyclic intermediates. XL. Studies on the acylation of lithiated bislactim ethers of cyclo-(L-Val-Ala-) and cyclo (L-Val-Gyl-)", see p. 785, abstract 150014r, & Liebigs Ann. chem. 1988, (8), 781-6.

Tetrahedron, vol. 39, No. 12, 1983, Pergamon Press, (Oxford, GB), U. Schollkopf, "Enantioselective synthesis of non-proteinogenic amino acids via metallated bis-lactim ethers of 2,5-diketopiperazines", pp. 2085-2091.

Liebags Annalen der Chemie, issue 11, Nov. 1988, VCH Verlagsgesellschaft mbH, (Weinheim, DE), U. Schollkopf et al: "Asymmetric synthesis of Boc-L-Val-(R-)-MePro-OMe, Boc-L-Val-(R)—Pro OMe, and of Boc-L-Val-(R)—MePhe-OMe and their analogues. A new stratgey for the synthesis of non-proteinogenic bipeptides", pp. 1025-1031.

Helvetica Chimica Acta, vol. 69, pp. 749-1534, Peter Wipf et al. "124. Kupplung von Peptiden mit C-terminalen x,x-disubstituierten x-Aminosauren via Oxazol-5 (4H)-one".

Journal of the American Chemical Society, vol 103, 1981, pp. 5991-7040, T. M. Balasubramanian, et al. "Synthesis and Acharacterization of the Major Component of Alamethicin", pp. 6127-6232.

*Primary Examiner*—Jose G. Dees
*Assistant Examiner*—B. Frazier
*Attorney, Agent, or Firm*—Oblon, Spivak, McClelland, Maier & Neustadt

[57] ABSTRACT

Process for producing dipeptides from non-proteinogenic amino acids with terminal carbon atoms.

3 Claims, No Drawings

PROCESS FOR THE PREPARATION OF DIPEPTIDES WITH C-TERMINAL NON-PROTEINOGENOUS AMINO ACIDS

DESCRIPTION

The present invention relates to a process for preparing dipeptides derived from non-proteinogenous amino acids.

The specific synthesis of peptides which contain non-proteinogenous amino acids entails stepwise synthesis of the desired peptides employing the unnatural amino acids and using conventional protective groups and activation methods.

In this strategy, the unnatural amino acids employed are obtained either by non-enantioselective synthesis and subsequent racemate resolution or by enantioselective synthesis using optically active auxiliaries.

Difficulties in forming the peptide linkage can occur especially when the α position of the unnatural amino acid is substituted by two sterically demanding radicals (Helv. Chim. Acta 69, (1986) 1153, J. Amer. Chem. Soc. 103 (1981) 6127).

It has now been found that certain dipeptides can be prepared in a straightforward manner.

The invention relates to a process for preparing dipeptides with C-terminal non-proteinogenous amino acids, of the formula I

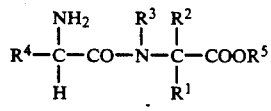

in which $R^1$ is a $C_1$–$C_8$-alkyl, phenyl or benzyl group, $R^2$ denotes a $C_1$–$C_8$-alkyl group which can be interrupted by —O—, —S—, —CO— or —CO—O—, or a phenyl or benzyl group, $R^3$ is a hydrogen atom or a $C_1$–$C_8$-alkyl group or represents together with $R^2$ the radicals —(CH$_2$)$_3$—, —(CH$_2$)$_4$— or —CH$_2$—CH=CH—CH$_2$—, and $R^4$ denotes a methyl, isopropyl, isobutyl, 2-butyl, t-butyl or benzyl radical, $R^5$ is a methyl or ethyl group, which comprises hydrolyzing a compound of the formula II

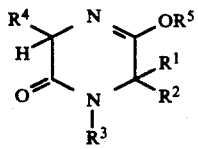

in which $R^1$ to $R^5$ have the stated meaning.

The hydrolysis of the compounds II to give the final products takes place especially well in dilute aqueous mineral acids in the presence of organic cosolvents such as methanol, ethanol, tetrahydrofuran, acetonitrile or dioxane. The mineral acids which are preferably used are HCl, HBr and HI. The reaction is normally carried out at from 0° to 40° C. The reaction takes 15 min to 6 h.

The compounds II can be obtained by selective partial acid-catalyzed cleavage of the compounds III

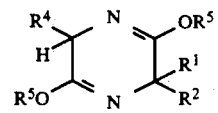

The selective partial acid-catalyzed cleavage is carried out by reacting the compounds III with one equivalent of acid in an inert aprotic solvent. Acids which should be particularly mentioned are HCl, HBr and HI, and Lewis acids such as trialkylsilyl halides or dialkoxyboron halides. Suitable solvents are diethyl ether, dibutyl ether, tetrahydrofuran, dioxane, dichloromethane, tetrachloromethane, toluene, cyclohexane and ethylene glycol dimethyl ether. The reaction is usually carried out at from 0° to 40° C. The reaction takes 15 min to 6 h.

The compounds II in which $R^3$ is hydrogen can be converted by base-induced alkylation with alkyl halides or alkyl sulfates into the compounds II in which $R^3$ is a $C_1$–$C_8$-alkyl group.

The compounds of the formula II in which $R^3$ is a hydrogen atom and $R^5$ is an ethyl group can be prepared especially well from the compounds of the formula IV

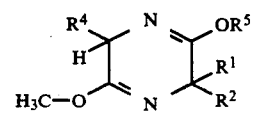

by demethylation with a trialkylsilyl iodide with 1–4 carbon atoms in the alkyl radicals. The reaction is expediently carried out at from 0° to −20° C. in an anhydrous halohydrocarbon as solvent and under an inert gas. The trialkylsilyl iodides which are preferably used are those of the formula

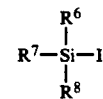

in which $R^6$–$R^8$ are $C_{1-4}$ alkyl radicals.

Because some of the compounds I in the form of the free bases readily form the corresponding diketopiperazines by ring closure, the salts of I produced in the hydrolysis are preferably converted by reaction with the acylating agents customary in peptide chemistry, such as benzyloxycarbonyl chloride, 9-fluorenylmethoxycarbonyl chloride or di-tert-butyl carbonate into the N-protected derivatives (cf. Houben-Weyl, Methoden der organischen Chemie, Vol. 15/1, G. Thieme Verlag, Stuttgart 1974) or reacted with activated amino-acid derivatives (cf. Houben-Weyl, Methoden der organischen Chemie, Vol. 15/2, G. Thieme Verlag, Stuttgart 1974) to give tripeptide derivatives.

The compounds I have two asymmetric carbon atoms which can have the (R) and (S) configuration and whose configuration can be identical or different.

The starting materials III required for the synthesis of the dipeptides are known, cf. Pure Appl. Chem. 55, 1799 (1983) Angew. Chem. 99, 137 (1987) and earlier publications in this series.

The compounds IV in which $R^5$ represents an ethyl group can be prepared particularly straightforwardly by reacting a compound of the formula V

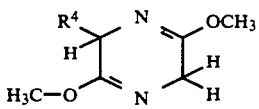

with a mono- or dialkylamine in the presence of a trialkyl borate or of another mild Lewis acid to give a compound of the formula VI

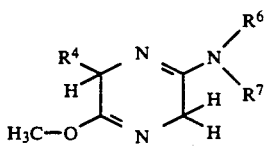

in which $R^6$ represents a hydrogen atom or a $C_1$–$C_6$-alkyl group and $R^7$ represents a $C_1$–$C_6$-alkyl group, removing the amine radical by hydrolysis and subsequently ethylating the hydrolysis product in the 6 position with triethyloxonium tetrafluoborate. The resulting mixed bislactim ethers of the formula VII

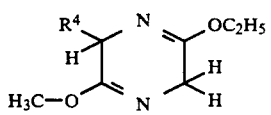

(VII=IV, $R^1=R^2=H$, $R^5=C_2H_5$) can subsequently be converted by single or double C-alkylation of their lithium salts into the intermediates IV.

Conversion of V into VI is preferably carried out by reacting V with a methanolic solution of about 1.5 equivalents of mono- or dialkylamine in the presence of catalytic quantities of a Lewis acid at from 20° to 60° C. The compounds VI are purified by distillation.

The conversion of VI into VII takes place in two steps. In the first step, the amino group is eliminated by hydrolysis. For this, VI is stirred in water at pH 6 to 9 at 50° to 100° C. The mixture is then extracted with a solvent such as halohydrocarbon or ethyl acetate, and the resulting monolactim ether is alkylated with triethyloxonium tetraborate (sic). The alkylation is carried out in a chlorohydrocarbon at room temperature and usually takes from 1 to 3 days. The alkylation is followed by neutralization of the solution and extraction of the compound VII.

The process according to the invention for preparing the α-alkyl-branched dipeptides is distinguished by the fact that the unnatural amino acid is built up on a lactim ether derivative, i.e. a masked dipeptide derivative, which can be obtained without difficulty. This chiral "auxiliary" II becomes part of the desired dipeptide. The invention makes it possible to cleave only one ether linkage in the compounds III and IV. Thus, surprisingly, the monolactim ether II is the very predominant product from III with one equivalent of acid. Any regional isomers which are produced are removed by chromatography or distillation. Compounds of the formula II can be obtained in a particularly straight-forward manner from IV by selective demethylation with trialkylsilyl iodide. I is obtained from II by selective hydrolysis with aqueous acid.

Compounds of the formula I and N-protected derivatives which can be prepared therefrom in a straightforward manner by reaction with the conventional acylating agents such as benzyloxycarbonyl chloride, 9-fluorenylmethoxycarbonyl chloride or di-tert-butyl dicarbonate ($(BOC)_2O$) are used as building blocks for synthesizing biologically active peptides. The process is suitable for preparing building blocks for peptides or peptide analogues which inhibit the enzyme renin, are active on oral intake and thus can be used for treating high blood pressure.

EXAMPLES a. BOC-L-Val-R-α MePhe-OMe 1.44 g of (2S,5R)-2,5-dihydro-2-isopropyl-3,6-dimethoxy-5-benzyl-5-methylpyrazine in 30 ml of diethyl ether were treated at room temperature with 25 ml of 0.2 N HCl in diethyl ether. After 2 h, the mixture was evaporated under reduced pressure. Distillation of the residue yielded 0.94 g (69%) of crude (2S,5R)-2,5-dihydro-2-isopropyl-6-methoxy-5-benzyl-5-methyl-3-pyrazinone, boiling point 170° C./0.005 torr.

50 ml of 0.1 N HCl were added to a solution of 0.35 g of the pyrazinone obtained above in 50 ml of acetonitrile. Reaction was then carried out with stirring at room temperature for 24 h. Working up initially entailed removal of unreacted pyrazinone by extraction with 3×30 ml of dichloromethane. The aqueous phase was adjusted to pH 9 with ammonia and extracted with dichloromethane (3×10 ml). The organic extract was dried over magnesium sulfate and evaporated to dryness under reduced pressure. 0.3 g of crude H-Val-R-αMePhe-OMe was obtained and was immediately converted by the conventional process with di-tert-butyl dicarbonate/triethylamine in dichloromethane into the BOC compound. Purification by chromatography on silica gel (elution with 1:3 ether/petroleum ether) yielded 0.35 g (90%) of BOC-L-Val-R-αMePhe-OMe, melting point 57° C.

2. BOC-L-Val-R-αMePro-OMe 0.45 g of (2S,5R)-2,5-dihydro-2-isopropyl-5-methyl-6-methoxypyrrolidino-3-pyrazinone in 20 ml of tetrahydrofuran were mixed with 30 ml of 3 N HCl at room temperature. Evaporation to dryness and reaction with di-tert-butyl dicarbonate in triethylamine yielded after purification by chromatography on silica gel (elution with 1:1 ether/petroleum ether) 0.43 g of BOC-L-Val-R-αMePro-OMe, melting point 92°–95° C.

The following were obtained analogously:

3. Methyl BOC-L-R-αMe-pipecolate; melting point 81°–85° C.;

4. Methyl BOC-L-Val-R-αMe-baikiate; melting point 31°–35° C.

5. BOC-L-Val-(D)-N-methyl-Me-Phe-OEt a) 0.3 g of (2R,5S)-2-benzyl-2,5-dihydro-3-ethoxy-5-isopropyl-6-methoxy-2-methylpyrazine was dissolved in 15 ml of absolute dichloromethane and cooled under argon to −10° C. Then 25 mg of iodine and 0.16 ml of trimethylsilyl iodide were added. After 3 h, the solution was allowed to warm to room temperature and was stirred at 22° C. for 14 h. 5 ml of ethanol and 5 ml of diethylamine were added and the mixture was then evaporated under reduced pressure and the residue was chromatographed on silica gel (ether, Rf=0.44). 0.29 g (91%) of (2R,5S)-2-benzyl-3- ethoxy-5-isopropyl-1,2,5,6-tetrahydro-2-methyl-6-pyrazinone, melting point 125° C., was obtained.

b) 0.25 g of the product obtained in a) was dissolved in 10 ml of tetrahydrofuran and, after addition of 7 mg of sodium hydride, stirred at room temperature for 1.5 h. After addition of 0.5 ml of dimethyl sulfate, the mixture was stirred for a further 10 h. Then 2 ml of dimethylamine and 4 ml of ethanol were added and the solvent was stripped off. Chromatography on silica gel (1:1 diethyl ether/petroleum ether, Rf=0.14) yielded 0.25 g (96%) of (2R,5S)-2-benzyl-3-ethoxy-5-isopropyl-1,2,5,6-tetrahydro-2-methyl-6-pyrazinone.

c) 0.2 g of the product obtained in b) was dissolved in 10 ml acetonitrile, and 2.7 ml of 1 N hydrochloric acid were added. The mixture was left to stand at room temperature for 5 h and then concentrated under reduced pressure. The residue was dissolved in 1.2 ml of triethylamine and 10 ml of dichloromethane, and 0.3 g of BOC anhydride was added. The mixture was stirred at room temperature for 12 h and then concentrated under reduced pressure. The residue was . . . (sic) by chromatography on silica gel (3:1 petroleum ether/diethyl ether, Rf=0.11). 0.26 g (85%) of product was obtained.

$C_{23}H_{36}N_2O_5$ (420.55); Calc.: C=65.69, H=8.63. Found: C=65.51, H=8.60.

6. (L)-N-BOC-Val-(D)-Me-Phe-OEt

The example was repeated without process step b). The final product was obtained in 83% yield, melting point 102° C.

We claim:

1. Process for preparing dipeptides with C-terminal non-proteinogenous amino acids, of the formula I

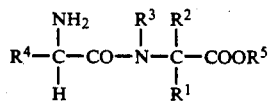

in which $R^1$ is a $C_1$–$C_8$-alkyl, phenyl or benzyl group, $R^2$ denotes a $C_1$–$C_8$-alkyl group which can be interrupted by —O—, —S—, —CO— or —CO—O—, or a phenyl or benzyl group, $R^3$ is a hydrogen atom or a $C_1$–$C_8$-alkyl group or represents together with $R^2$ the radicals —(CH$_2$)$_3$—, —(CH$_2$)$_4$— or —CH$_2$—CH=CH—CH$_2$—, and $R^4$ denotes a methyl, isopropyl, isobutyl, 2-butyl, t-butyl or benzyl radical, $R^5$ represents a methyl or ethyl group, characterized in that a compound of the formula II

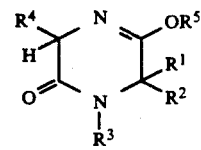

in which $R^1$ to $R^5$ have the stated meaning, is hydrolyzed.

2. Process according to claim 1, characterized in that the compounds of the formula II in which $R^3$ denotes hydrogen or a $C_1$–$C_8$-alkyl radical are obtained by selective partial cleavage of compounds of the formula III

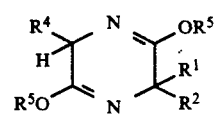

in which $R^1$, $R^2$, $R^4$ and $R^5$ have the meaning specified in claim 1, and subsequent N-alkylation where appropriate.

3. Process according to claim 1, characterized in that the compounds of the formula II ($R^3$=H) are obtained by demethylation of compounds of the formula IV

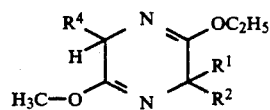

in which $R^1$, $R^2$ and $R^4$ have the meaning specified in claim 1, with a trialkylsilyl iodide.

* * * * *